United States Patent [19]
Akin et al.

[11] Patent Number: 4,976,257
[45] Date of Patent: Dec. 11, 1990

[54] HYPEREXTENSION BRACE

[75] Inventors: Timothy W. Akin, 1620 Clinton Ave., Alameda, Calif. 94501; Rudi Bindi, Belle Air Beach, Fla.

[73] Assignee: Timothy W. Akin

[21] Appl. No.: 393,782

[22] Filed: Aug. 15, 1989

[51] Int. Cl.$^5$ ................................................ A61F 5/02
[52] U.S. Cl. ........................................ 128/78; 128/75; 128/89 R; 128/82
[58] Field of Search ...................... 128/68, 69, 75, 78, 128/DIG. 15, 82, 83, 84 R, 85, 89 R, 90, 96.1, 99.1, 100.1, 101.1, 117.1

[56] References Cited

U.S. PATENT DOCUMENTS

| | | | |
|---|---|---|---|
| Re. 31,564 | 4/1984 | Hendricks . | |
| 2,886,031 | 3/1959 | Robbins | 128/78 |
| 3,274,996 | 9/1966 | Jewett . | |
| 4,173,973 | 11/1979 | Hendricks . | |
| 4,230,101 | 10/1980 | Gold | 128/78 |
| 4,245,627 | 1/1981 | Mignard | 128/78 |
| 4,640,269 | 2/1987 | Goins | 128/78 |
| 4,715,362 | 12/1987 | Scott | 128/78 |

FOREIGN PATENT DOCUMENTS 83462  2/1895  Fed. Rep. of Germany ...... 128/78

Primary Examiner—Richard J. Apley
Assistant Examiner—Lynne A. Reichard
Attorney, Agent, or Firm—Glen R. Grunewald

[57] ABSTRACT

A hyperextension brace comprising anterior brace structure including an anterior brace portion of unitary construction and formed of flexible material, an enlogated, rigid reinforcement member attached to the anterior brace portion by fasteners, back brace structure, and securement structure for securing the anterior brace structure and back brace structure to a human body.

12 Claims, 5 Drawing Sheets

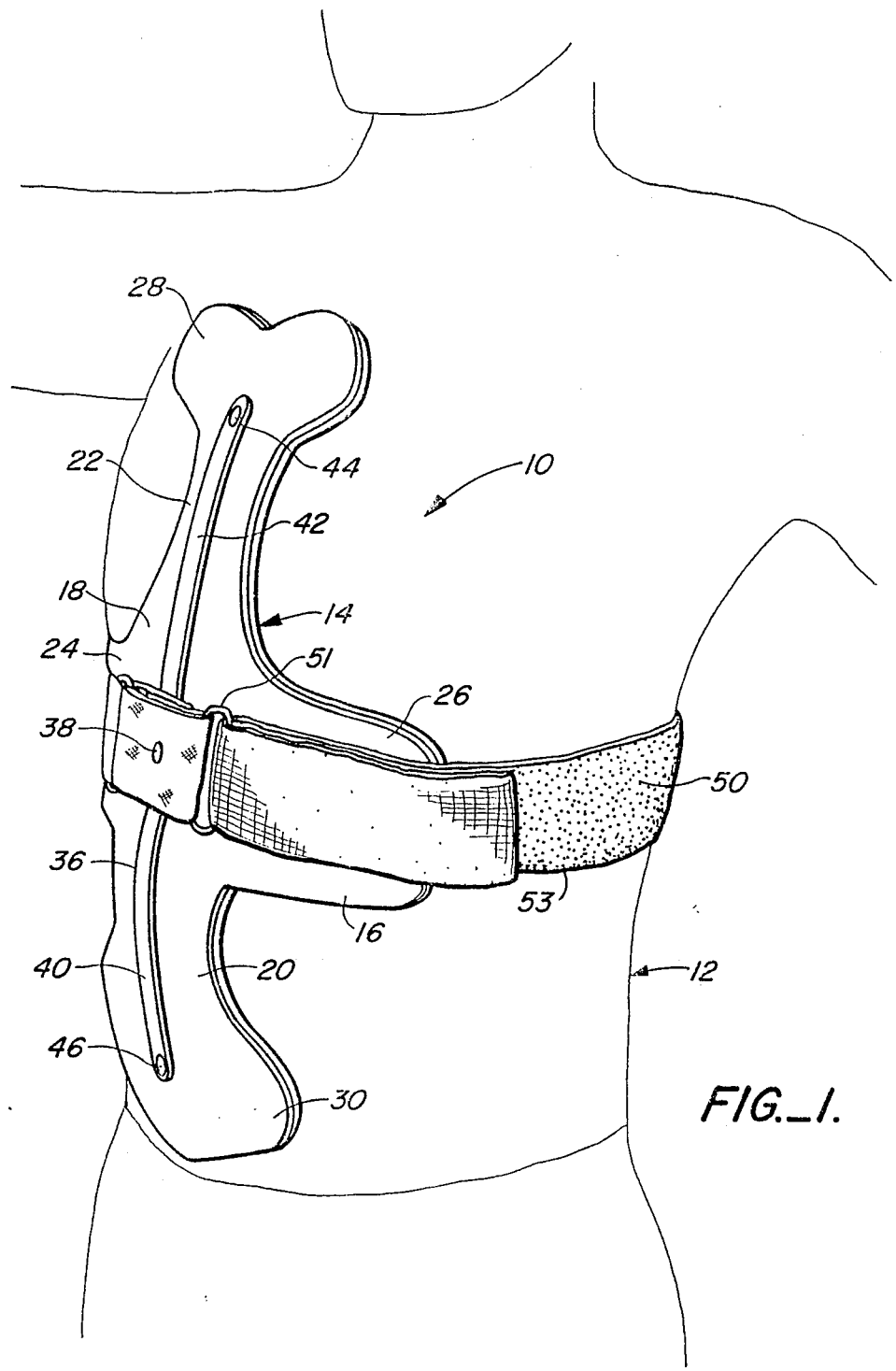
FIG._1.

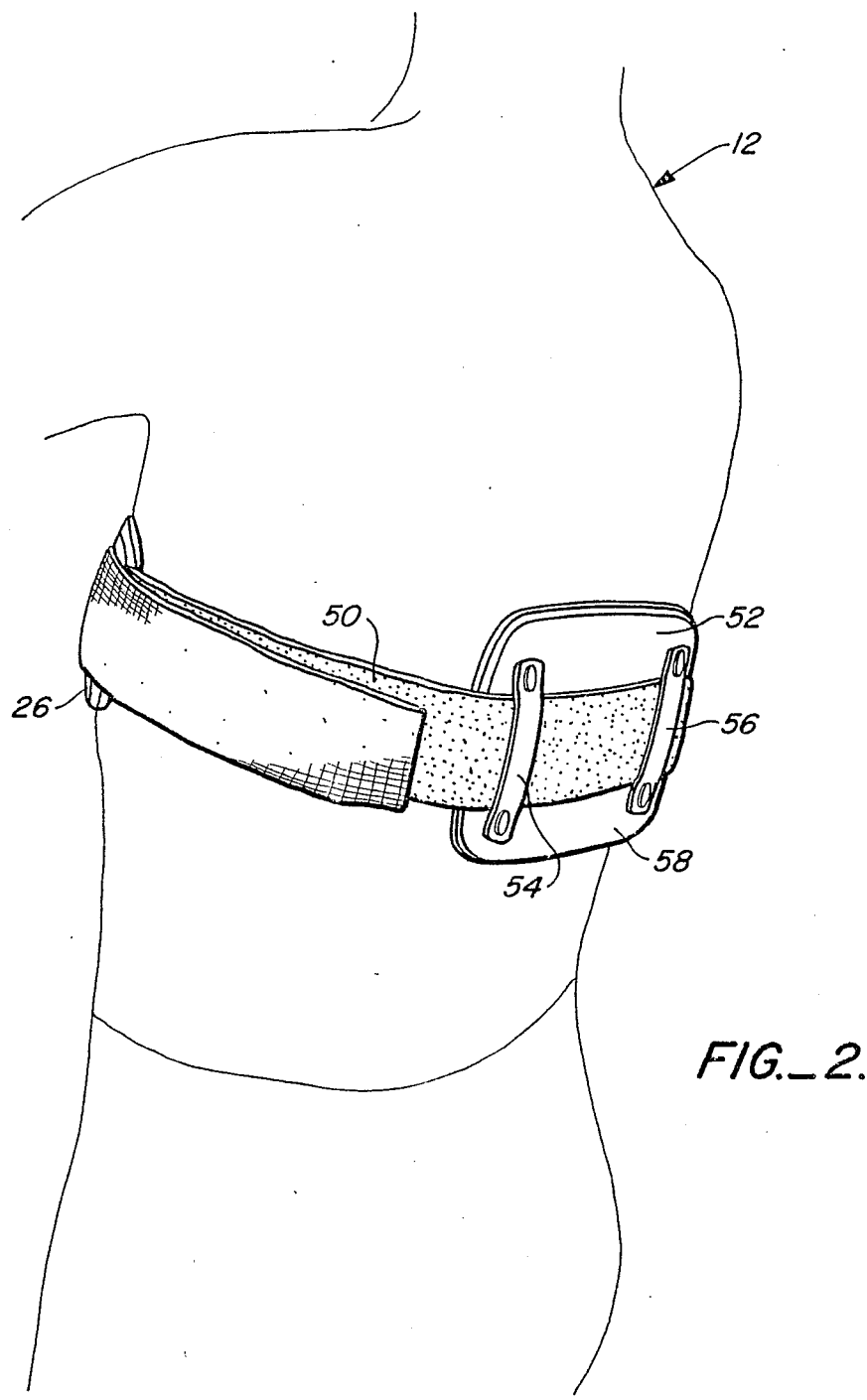
FIG._2.

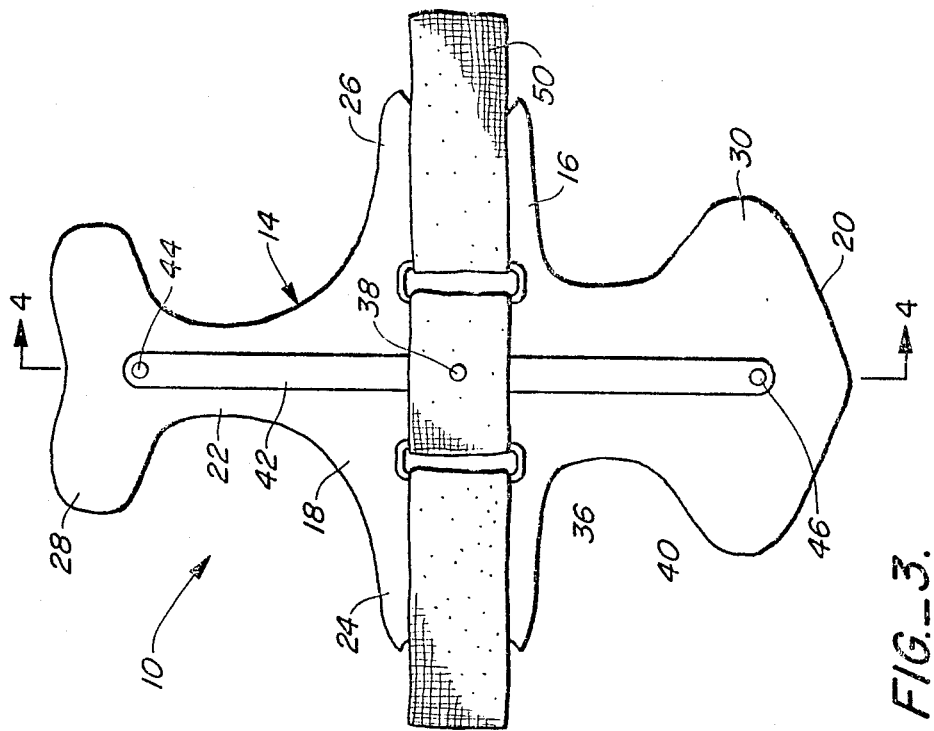
FIG._3.
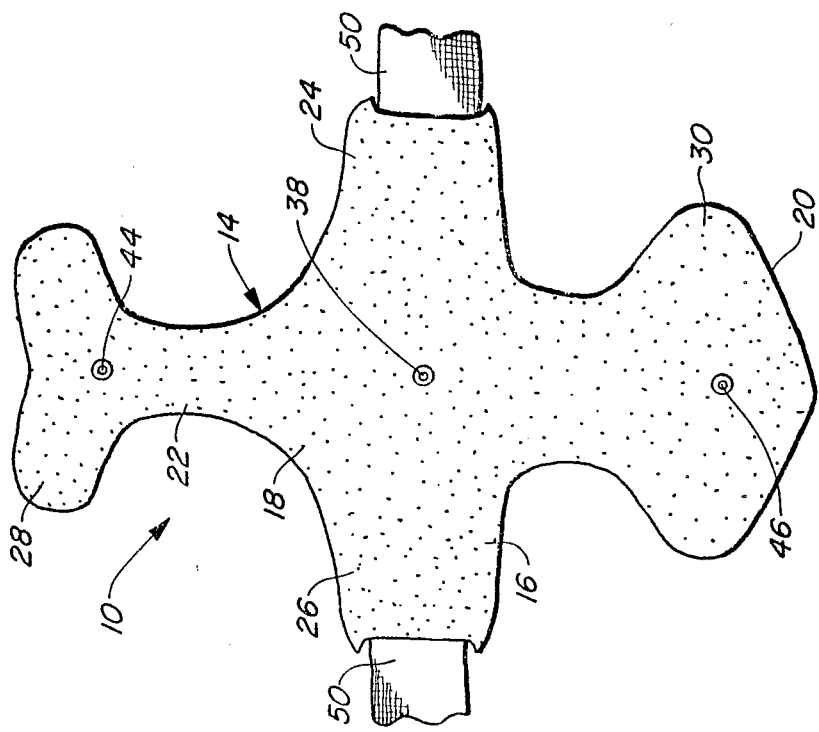
FIG._3A.

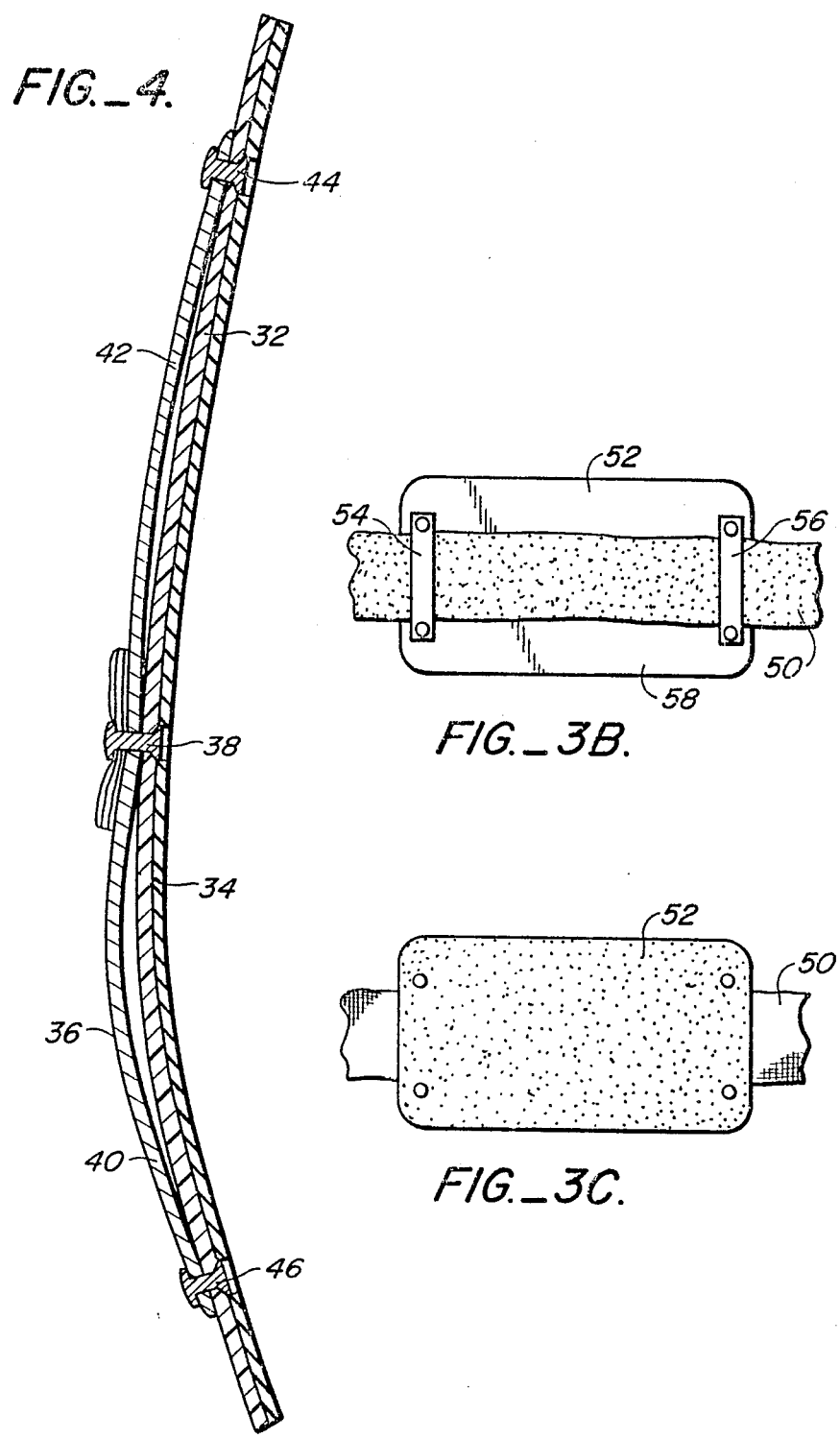

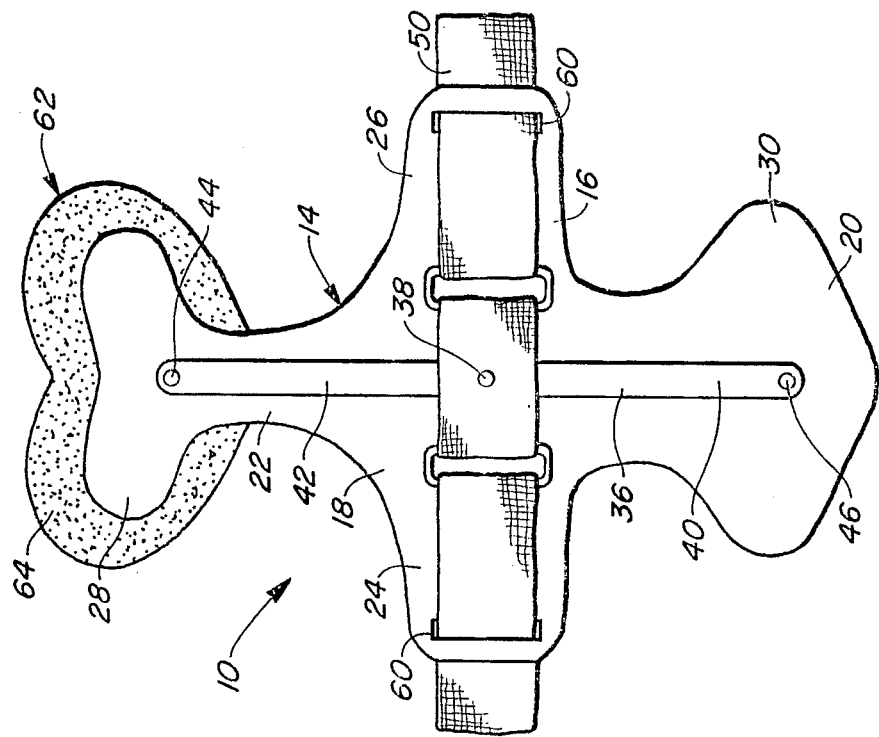
FIG._5.
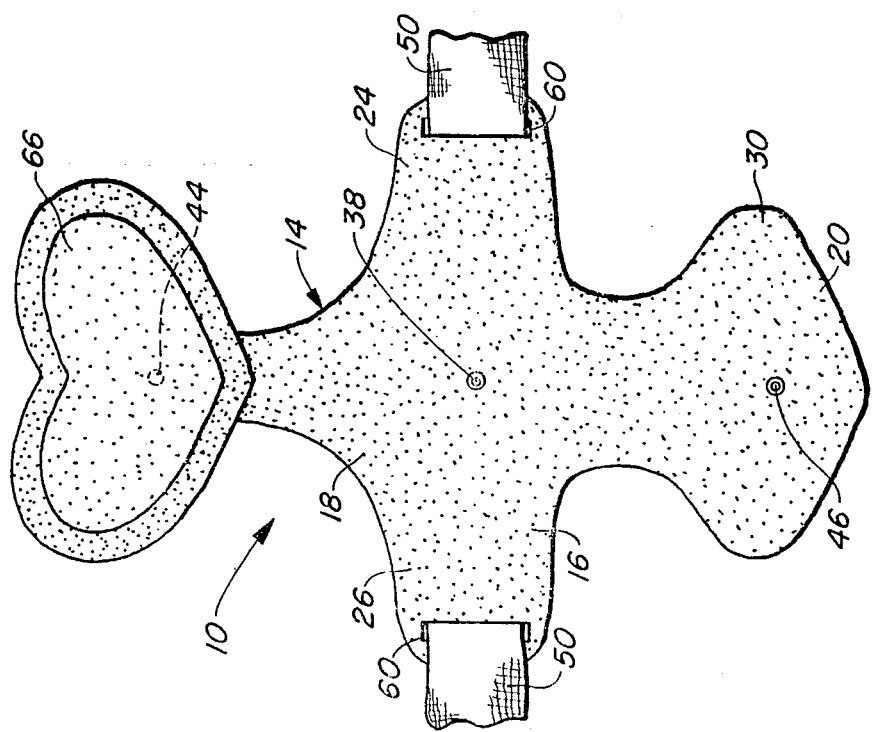
FIG._5A.

HYPEREXTENSION BRACE

TECHNICAL FIELD

This invention relates to a brace structure which applies forces to a human body to hyperextend the back. The brace has particular application by patients suffering pain and discomfort due to a disease or deformity of the spinal area.

BACKGROUND ART

Hyperextension braces are well known in the art, examples being the braces shown in U.S. Pat. Nos. 3,274,996, 4,173,973 and Re. 31,564.

Prior art hyperextension braces have been characterized by their relative complexity and high expense. Such prior art braces also commonly tend to be heavy and bulky, characteristics which are inimical to extended usage by a patient.

It will be appreciated that it is highly desirable to provide some means whereby a brace structure may be adjusted or adapted for use by patients of differing sizes and shapes, and in fact, various schemes have been employed to provide brace adjustability. However, introduction of this capability in the past has resulted in increased cost, complexity, weight and bulkiness of the brace structure. Then too, adjustable hyperextension braces often lose proper adjustment and require the use of tools to accomplish required adjustment.

DISCLOSURE OF INVENTION

The hyperextension brace of the present invention is of relatively simple, inexpensive and compact construction. The brace may be readily modified to adapt it for use by patients of different sizes and body types. The brace is light-weight and comfortable to wear, yet it provides a patient with positive support to alleviate discomfort and pain.

The hyperextension brace of the present invention incorporates anterior brace means including an anterior brace portion of unitary construction and formed of flexible sheet material. The anterior brace portion has a central segment, a first pair of opposed arms projecting from the central segment along a first axis, and a second pair of opposed arms projecting from the central segment along a second axis substantially perpendicular to the first axis.

One of the first pair of opposed arms is enlarged at the distal end thereof to form a sternal pad element and the other of the first pair of opposed arms is enlarged at the distal end thereof to form a pubic pad element.

An elongated rigid reinforcement member is disposed along the first axis and extends across the central segment, terminating at opposed reinforcement member ends located at the sternal pad element and a pubic pad element.

Attachment means is provided for fixably attaching the reinforcement member to the anterior brace portion at the central segment and at each of the arms of the first pair of opposed arms whereby the sternal pad element, the pubic pad element and the central segment are maintained in substantially fixed relationship relative to one another.

The attachment means comprises a plurality of spaced fasteners and the reinforcement member includes two integral reinforcement member components. One of the reinforcement member components extends from a first fastener located at the central segment to a second fastener located at the sternal pad element. The other of the reinforcement member components extends from the first fastener to a third fastener located at the pubic pad element.

In the illustrated preferred embodiment of the invention, each of the reinforcement member components is of a generally arcuate configuration whereby the components are spaced from the anterior brace portion at locations between the fasteners.

Other features, advantages and objects of the present invention will become apparent with reference to the following detailed description and accompanying drawings.

BRIEF DESCRIPTION OF DRAWINGS

FIG. 1 is a perspective, generally frontal view of a preferred embodiment of hyperextension brace constructed in accordance with the teachings of the present invention positioned on a human body;

FIG. 2 is a view similar to FIG. 1 but taken from the rear of the brace and human body;

FIG. 3 is a frontal view of the brace specifically illustrating the anterior brace mean and portion of the securement means thereof;

FIG. 3A is a view similar to FIG. 3 as seen from the rear of the brace;

FIGS. 3B and 3C are detail views of the back brace means.

FIG. 4 is a cross-sectional longitudinal view of the brace;

FIG. 5 is a view similar to FIG. 3 but illustrating an alternative embodiment of the brace; and FIG. 5A is a view similar to that of FIG. 3A but illustrating the embodiment of the brace shown in FIG. 5.

MODES FOR CARRYING OUT THE INVENTION

Referring now to FIGS. 1-4, a preferred form of hyperextension brace constructed in accordance with the teachings of the present invention is illustrated and generally designated by reference numeral 10. In FIGS. 1 and 2, brace 10 is illustrated as being disposed on a human body 12.

Brace 10 incorporates anterior brace means 14 including an anterior brace portion 16 having a central segment 18. A first pair of opposed arms 20, 22 projects from central segment 18 along a first axis. A second pair of opposed arms 24, 26 projects from the central segment 18 along a second axis substantially perpendicular to the first axis.

Arm 22 is enlarged at the distal end thereof to form a sternal pad element 28. Arm 20 is enlarged at its distal end to form a pubic pad element 30.

As may perhaps best be seen with reference to FIG. 4, the sheet material of which the anterior brace portion is constructed is a multi-laminate material including an outer layer 32 of solid plastic and an inner layer of padding 34 adhesively secured or heat-bonded to the outer layer 32. In the illustrated embodiment of the invention shown in FIGS. 1-4, the outer layer may, for example, be formed of polyethylene and has a substantially uniform thickness of about three-sixteenth in. The inner layer may be formed of water repellant plastic foam of the type sold under name Plastazote and having a substantially uniform thickness of about one-quarter in. Sheet material of the above-described type has a degree of flexibility.

An elongated, rigid reinforcement member 36 constructed, for example, of stainless steel or aluminum bar material or the like is disposed along the first axis. Reinforcement member 36 extends across central segment 18 and terminates at opposed reinforcement member ends located at the sternal pad element 28 and the pubic pad element 30.

The reinforcement member 36 is fixedly attached to the anterior brace portion 16 by attachment means in the form of fasteners such as rivets. A first such fastener 38 is located at the central segment 18.

Reinforcement member 36 includes two integral reinforcement member components 40, 42. Reinforcement member component 42 extends from first fastener 38 to a second fastener 44 located at sternal pad element 28. Reinforcement member component 20 extends from the first fastener 38 to a third fastener 46 located at pubic pad element 30.

Each of the reinforcement member components 40, 42 is of a generally arcuate configuration and spaced from the anterior brace portion 16 at locations between the fasteners. It will thus be seen that each reinforcement member component will resist outward flexing of its associated pad element to a greater degree than would be the case if the reinforcement member components were in continuous contact with their respective arms 20, 22.

Securement means is provided for securing the brace to human body 12 and includes a strap 50 affixed to central segment 18 of anterior brace means 14 by first fastener 38. Thus, reinforcement member 36 is sandwiched between the strap and the anterior brace portion.

From first fastener 38 strap 50 extends along the second axis over second pair of opposed arms 24, 26. In the arrangement shown in FIGS. 1-4, the strap extends over and around the distal ends of arms 24, 26 alongside human body 12 and to back brace means 52, said back brace means essentially being in the form of a generally flat plate. The back brace means may, if desired, be formed of the same material as anterior brace portion 16. To maintain the strap 50 in position relative to back brace means 52, the back brace means may incorporate a pair of guides 54, 56 attached to the plate component 58 of the back brace means, as shown in FIGS. 3B-3C.

Insofar as the present invention is concerned, the strap 50 may be of unitary construction or, as shown, include several strap components secured together by an suitable connectors. The ends of the strap 50 preferably incorporate securement material of the type sold under the trademark Velcro whereby the ends of the strap may be readily manually secured or separated. In the illustrated preferred embodiment of FIGS. 1-4, the strap components pass through connectors in the form of loops 51. At least one of the strap components has a free end 53. With this arrangement the brace may readily be opened or closed by the user from the front.

Opposed arms 24, 26 are adapted to bend, as shown, into general conformance with human body 12 when strap 50 is tightened. Also, the arms 24, 26 are of sufficient length and the plate component 58 of sufficient size to enable the strap 50 to extend along generally straight lines to the back brace means 52 when the brace is secured in position. This enables force to be directly applied to the back brace means along the straps by the second pair of opposed arms.

When properly positioned on a patient, brace 10 establishes a primary contact with the patient's body at three points or locations. These primary points of contact are at the sternal pad element 28, pubic pad element 30 and back brace means 52. The reinforcement member component 40 maintains the pubic pad element, the sternal pad element and the central segment in substantially fixed relationship to one another, and in such relationship the pubic and sternal pad elements are normally disposed in a plane offset inwardly from the central segment 18.

The desired configuration may be obtained by manually bending the reinforcement member 36 over the back of a chair or the like prior to applying the brace to the patient. Additionally, the sternal pad element and pubic pad element may be readily shaped to a desired contour to fit a particular patient. This may be accomplished by heating the pad elements with a heat gun and manually shaping the pad elements to the desired contour.

Yet another advantage of the present arrangement resides in the fact that the ends of elongated rigid reinforcement member 36 are disposed inwardly of the outermost distal edges of the pad elements, for example, one to one and a quarter in from the outermost distal edges. Thus, the pad elements may be cut at locations spaced from the reinforcement member ends to reduce the size of the pad elements or permanently modify the outer configurations thereof.

Referring now to FIGS. 5 and 5A, an alternative embodiment of the invention is illustrated. This alternative embodiment differs from that of FIGS. 1-4 in two respects. First, the arms 24, 26 define openings 60 at the ends thereof to accommodate strap 50 and maintain the strap in engagement with the second pair of opposed arms. The second difference lies in the fact that the brace includes a supplemental cushion 62 attached to sternal pad element 28 as by means of releasable securement material such as that sold under the trademark Velcro. If desired, a supplemental cushion could be attached to pubic pad element 30 in precisely the same manner.

The supplemental cushion 62 includes a relatively rigid primary portion 64 which may, for example, be formed of the same plastic material as outer layer 32 of anterior brace means 14. An inner pad 66 of material such as that employed to form inner layer of padding 34 is bonded or otherwise attached to the primary portion 64. A supplemental cushion may be employed when one wishes to increase the contact area between one or both of the pad elements and the human body. If desired, the brace may be made available in several different sizes.

We claim:

1. A hyperextension brace for use on a human body, said brace comprising, in combination:
   anterior brace means including an anterior brace portion of unitary construction and formed of flexible sheet material, said anterior brace portion having a central segment, a first pair of opposed arms projecting from said central segment along a first axis and a second pair of opposed arms projecting from said central segment along a second axis substantially perpendicular to said first axis, one of said first pair of opposed arms enlarged at the distal end thereof to form a sternal pad element and the other of said first pair of opposed arms enlarged at the distal end thereof to form a pubic pad element, an elongated, rigid reinforcement member disposed along said first axis extending across said central segment and terminating at opposed reinforcement member ends located at said sternal pad element and said pubic pad element, and attachment means for fixedly attaching said reinforcement member to said anterior brace portion at said central segment and at each of the arms of said first pair of opposed arms whereby said sternal pad element, said pubic pad element and said central segment are maintained in substantially fixed relationship relative to one another;

securement means for securing said brace to a human body and including a strap connected to said anterior brace portion central segment and extendable along said second axis over said second pair of opposed arms, said strap when tightened about said human body adapted to bend the arms of said second pair of opposed arms into general conformance with said human body; and back brace means attached to said strap for retention by said strap on said human body.

2. The hyperextension brace according to claim 1 wherein said attachment means comprises a plurality of spaced fasteners and wherein said reinforcement member includes two integral reinforcement member components, one of said reinforcement member components extending from a first fastener located at said central segment to a second fastener located at said sternal pad element, and the other of said reinforcement member components extending from said first fastener to a third fastener located at said pubic pad element.

3. The hyperextension brace according to claim 2 wherein each of said reinforcement member components is of a generally arcuate configuration and spaced from said anterior brace portion at locations between said fasteners.

4. The hyperextension brace according to claim 1 wherein said sheet material is a multi-laminate material including an outer layer of solid plastic and an inner layer of padding bonded to said outer layer.

5. The hyperextension brace according to claim 4 wherein said outer layer of solid plastic has a substantially uniform thickness of about three-sixteenth in.

6. The hyperextension brace according to claim 5 wherein said outer layer is formed of polyethylene.

7. The hyperextension brace according to claim 4 wherein said inner layer is formed of water repellant plastic foam material.

8. The hyperextension brace according to claim 1 wherein said elongated rigid reinforcement member ends are located and attached to said pad elements and spaced inwardly of the outermost distal edges of said pad elements whereby said pad elements are adapted to be cut at locations spaced from said reinforcement member ends to reduce the size of said pad elements.

9. The hyperextension brace according to claim 1 wherein said second pair of opposed arms define openings at the ends thereof to accommodate said strap and maintain said strap in engagement with said second pair of opposed arms.

10. The hyperextension brace according to claim 1 additionally comprising a supplemental cushion releasably attachable to at least one of said pad elements.

11. The hyperextension brace according to claim 2 wherein said strap is affixed to said central segment by said first fastener.

12. The hyperextension brace according to claim 1 wherein the second pair of opposed arms are of sufficient length to enable the strap to extend along generally straight lines to said back brace means whereby force is directly applied to said back brace means along said strap by said second pair of opposed arms.

* * * * *